United States Patent [19]

Strike et al.

[11] 3,975,421

[45] Aug. 17, 1976

[54] 15-SUBSTITUTED 11α-CYANO-PROSTAGLANDINS AND RELATED COMPOUNDS

[75] Inventors: Donald P. Strike, St. Davids; Wenling Kao, Devon, both of Pa.

[73] Assignee: American Home Products Corporation, New York, N.Y.

[22] Filed: Sept. 5, 1974

[21] Appl. No.: 503,214

[52] U.S. Cl............................. 260/464; 260/340.9; 424/278; 424/304
[51] Int. Cl.².............. C07C 121/46; C07C 121/48
[58] Field of Search ................................. 260/464

[56] References Cited

UNITED STATES PATENTS

| | | | |
|---|---|---|---|
| 3,344,148 | 9/1967 | Dietrich et al.................. | 260/340.9 |
| 3,816,415 | 6/1974 | Fauran et al................. | 260/340.9 X |
| 3,845,042 | 10/1974 | Strike et al. .................... | 260/464 X |
| 3,853,951 | 12/1974 | Bernady et al.............. | 260/340.9 X |

*Primary Examiner*—Joseph Paul Brust
*Attorney, Agent, or Firm*—Robert Wiser

[57] ABSTRACT

11α-Cyano-15-substituted $PGE_1$ analogs, related compounds and intermediates thereto are disclosed. The final products have bronchodilatory, or anti-inflammatory activity.

4 Claims, 2 Drawing Figures

FIGURE 1

FIGURE 2

15-SUBSTITUTED 11α-CYANO-PROSTAGLANDINS AND RELATED COMPOUNDS

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation, the ability to reduce gastric secretion, to modify muscle tone, as well as the ability to raise or lower blood pressure.

Our Belgian Patent No. 803,854, published Feb. 21, 1974, discloses some 11-cyano substituted prostaglandins (prostanoic acid numbering system). The present invention discloses 11-cyano prostaglandins which differ from those compounds in the degree of side chain unsaturation, as well as, in a number of cases, the identity of the substituent in the 15-position.

SUMMARY OF THE INVENTION

The invention sought to be patented in a first composition aspect resides in the concept of a prostaglandin of the formula:

wherein X is

; R is hydrogen; and A is a cis double bond and B is a trans double bond, A is a single bond and B is a trans double bond, or A is a single bond and B is a single bond; or X is ; R is hydrogen, lower alkyl of from 1 to about 6 carbon atoms, alkali metal, or a pharmaceutically acceptable cation derived from ammonia or a primary amine; and A is a cis double bond, and B is a trans double bond; A is a single bond, and B is a trans double bond; or A is a single bond and B is a single bond.

The tangible embodiments of the first composition aspect of the invention possess the inherent general physical properties of being solids or clear to yellow oils, in the acid form are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the first composition aspect of the invention possess when X is >C=O the inherent applied use characteristic of exerting bronchodilating effects upon administration to warm-blooded animals as evidenced by pharmacological evaluation according to standard test procedures, and when X is are useful in the synthesis of compounds of Formula I wherein X is >C=O.

The invention sought to be patented in a first subgeneric aspect of the first composition aspect of the invention resides in the concept of a prostaglandin having the formula:

wherein A, B and R are as defined for Formula I.

The invention sought to be patented in a second subgeneric aspect of the first composition aspect of the invention resides in the concept of a prostaglandin of the structure:

wherein A and B are as defined for Formula I.

The invention sought to be patented in its second composition aspect resides in the concept of a prostaglandin of the formula:

wherein B is a trans double bond or a single bond.

The tangible embodiments of the second composition aspect of the invention possess the inherent general physical properties of being either solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the second composition aspect of the invention possess the inherent applied use characteristic of being intermediates in the synthesis of compounds of Formula I.

The invention sought to be patented in its third composition aspect resides in the concept of a prostaglandin having the formula:

III wherein R is hydrogen, lower alkyl of from 1 to about 6 carbon atoms, alkali metal, or a pharmacologically acceptable cation derived from ammonia or a basic amine.

The tangible embodiments of the third composition aspect of the invention possess the inherent general physical properties in the acid form of being crystalline solids, are substantiallly insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the third composition aspect of the invention possess the inherent applied use characteristic of exerting bronchodilating effects upon administration to warm-blooded animals as evidenced by pharmacological evaluation according to standard test procedures.

The invention sought to be patented in a fourth composition aspect resides in the concept of a prostaglandin of the formula:

IV wherein Y is and R is hydrogen, lower alkyl of from 1 to about 6 carbon atoms, alkali metal, or a pharmaceutically acceptable cation derived from ammonia or a basic amine.

The tangible embodiments of the fourth composition aspect of the invention possess the inherent general physical properties in the acid form of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the fourth composition possess the inherent applied use characteristic when Y is >C=O of exerting bronchodilating effects upon administration to warm-blooded animals, and when Y is of exerting anti-inflammatory effects upon administration to warm-blooded animals.

The invention sought to be patented in a first subgeneric aspect of the fourth composition aspect of the invention resides in the concept of a prostaglandin of the formula:

IVa wherein R is as defined for Formula IV.

The invention sought to be patented in a second subgeneric aspect of the fourth composition aspect of the invention resides in the concept of a prostaglandin of the formula:

IVb wherein R is as defined for Formula IV.

The invention sought to be patented in its fifth composition aspect resides in the concept of a prostaglandin of the formula:

V wherein X is >C=O and R⁴ is lower alkyl and R⁵ is lower alkanoyl; or X is and R⁴ and R⁵ are hydrogen, or R⁴ is lower alkyl and R⁵ is lower alkanoyl.

The tangible embodiments of the fifth composition aspect of the invention possess the inherent general physical properties of being crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the fifth composition aspect of the invention possess the inherent applied use characteristic of being intermediates in the synthesis of compounds of Formula I.

The invention sought to be patented in a first subgeneric aspect of the fifth composition aspect of the invention resides in the concept of a prostaglandin of the formula:

Va wherein R⁴ and R⁵ are as defined for Formula V.

The invention sought to be patented in a second subgeneric aspect of the fifth composition aspect of the invention resides in the concept of a prostaglandin of the formula:

Vb wherein R⁴ and R⁵ are as defined for Formula V.

DESCRIPTION OF THE PREFERRED EMBODIMENTS

Figure 1:
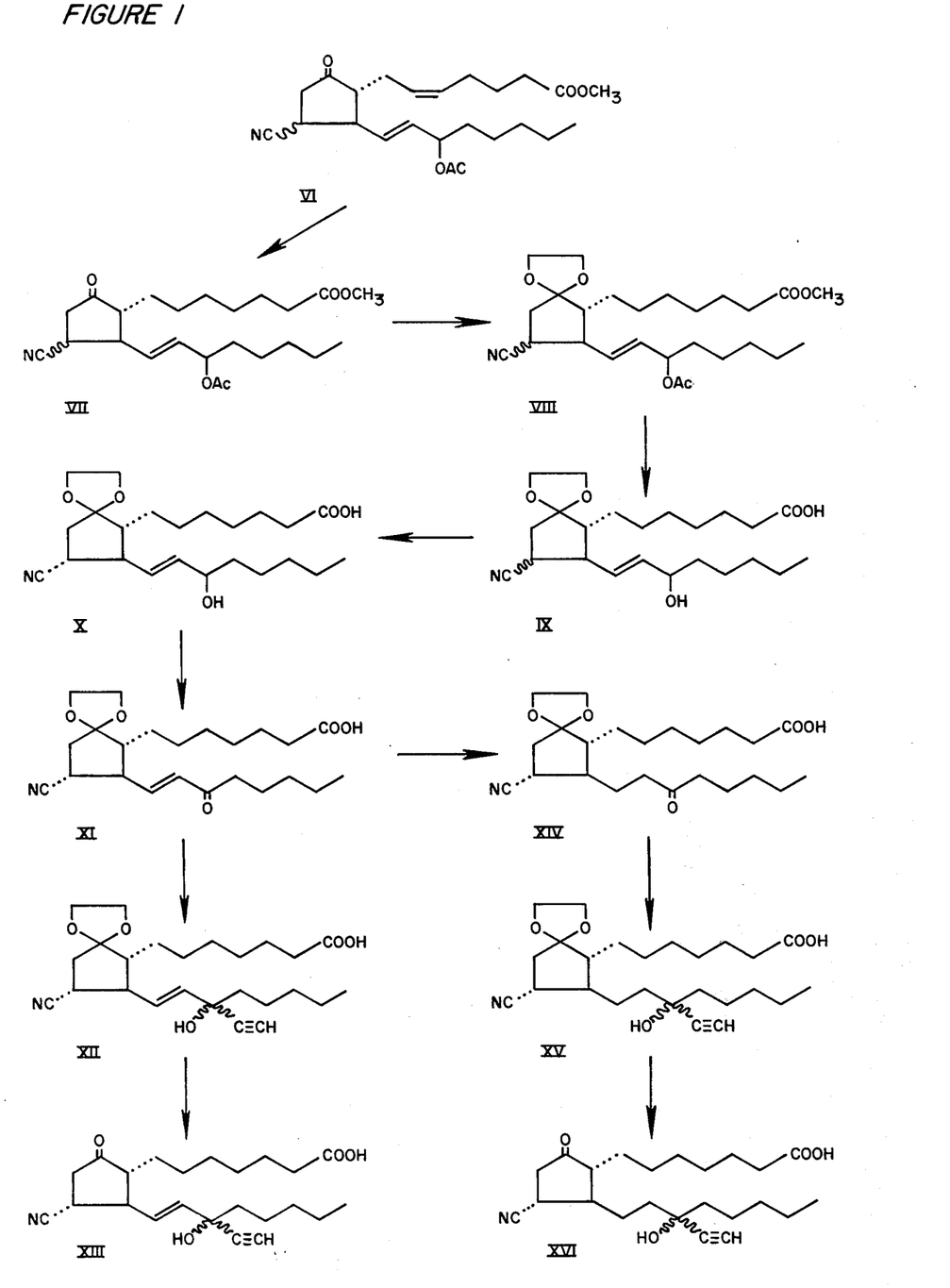

In describing the synthesis of the compositions of Formulas I, II and V, wherein A is a single bond, reference will be made to FIG. 1 wherein the formulae representing the specific embodiments are assigned Roman numerals for the purposes of identification. FIG. 1 illustrates the synthesis of 3α-cyano-2β-[(3RS)-3-ethynyl-3-hydroxyoctyl]-5-oxo-1α-cyclopentaneheptanoic acid (XVI), 8α-cyano-7β-[(3RS)-3-ethynyl-3-hydroxyoctyl]-1,4-dioxaspiro-[4.4]nonane-6α-heptanoic acid (XV), 3α-cyano-2β-[(3RS)-3-ethynyl-3-hydroxy-trans-1-octenyl]-5-oxo-1α-cyclopentaneheptanoic acid (XIII), and 8α-cyano-7β-[(3RS)-3-ethynyl-3-hydroxy-trans-1-octenyl]-1,4-dioxaspiro[4.4]nonane-6α-heptanoic acid (XII) all specific embodiments of Formula I; of 8α-cyano-7β-(3-oxo-octyl)-1,4-dioxaspiro[4.4]-nonane-6α-heptanoic acid (XIV), and 8α-cyano-7β-(3-oxo-trans-1-octenyl)-1,4-dioxaspiro[4.4-]nonane-6α-heptanoic acid (XI) both specific embodiments of Formula II; and of 8α-cyano-7β-[(3R)-3-hydroxy-trans-1-octenyl]-1,4-dioxaspiro[4.4]nonane-6α-heptanoic acid (X), (8RS)-8-cyano-7β-[(3R)-3-hydroxy-trans-1-octenyl]-1,4-dioxaspiro[4.4]nonane-6α-heptanoic acid (IX), (8RS)-8-cyano-7β-[(3R)-3-hydroxy-trans-1-octenyl]-1,4-dioxaspiro[4.4]nonane-6-heptanoic acid, methyl ester, acetate (VIII), and (3RS)-3-cyano-2β-[(3R)-3-hydroxy-trans-1-octenyl]-5-oxo-1α-cyclopentaneheptanoic acid, methyl ester, acetate (VII) all specific embodiments of Formula V.

The starting material for the preparation of VII, 7-((3RS)-3-cyano-2β-[(3R)-3-hydroxy-trans-1-octenyl]-5-oxo-1α-cyclopentyl)-cis-5-heptenoic acid, methyl ester, acetate (VI) is prepared as described in Belgian Patent 803,854, published Feb. 21, 1974. Hydrogenation of VI in the presence of tris(triphenylphosphine) rhodium (I) chloride at atmospheric pressure and room temperature until 1 equivalent of hydrogen is absorbed gives VII. VII may, if desired, be purified by elution chromatography on silica.

If VII is treated with a mixture of benzene and ethylene glycol in the presence of a catalytic amount of p-toluene sulfonic acid at the reflux temperature of the solvent and with removal of water, VIII is obtained. If desired, VIII may be isolated by elution chromatography on silica. Treatment of VIII with sodium hydroxide in dilute solution in aqueous methanol gives IX.

If IX is treated with potassium t-butoxide in solution in t-butanol, X is obtained. If desired, X may be isolated by elution chromatography on silica. Oxidation of X with Jones reagent gives XI. Treatment of XI with ethynyl magnesium bromide gives XII.

Treatment of XII with perchloric acid in aqueous tetrahydrofuran gives XIII. If desired, XIII may be isolated by elution chromatography on silica. If XI is treated with hydrogen in the presence of a 10% palladium on charcoal catalyst until 1 equivalent of hydrogen is absorbed, XIV is produced. If desired, XIV may be isolated by elution chromatography on silica. Treatment of XIV with ethynyl magnesium bromide gives XV. Treatment of XV with perchloric acid in aqueous tetrahydrofuran gives XVI. If desired, XVI may be isolated by elution chromatography on silica.

The preparation of the 15 epimer of VI (prostanoic acid numbering) is similarly taught by Belgian Patent 803,854 referenced hereinabove. The use of this epimer in the preparation of the 15 epimers of the compounds of Formula V illustrated will be obvious to one skilled in the art. Similarly the use of standard methods to convert the methyl ester, acetate illustrated to the other esters contemplated as part of the invention will be obvious. For example, VI or its epimers may be hydrolyzed to the free hydroxylic acid. This may then be esterified on the acid function by diazoalkanes, as described hereinbelow for the synthesis of esters of Formula I, and then the hydroxyl group esterified by standard techniques, for example by treament with alkanoyl halides, such as propanoyl chloride, and the like.

Figure 2:
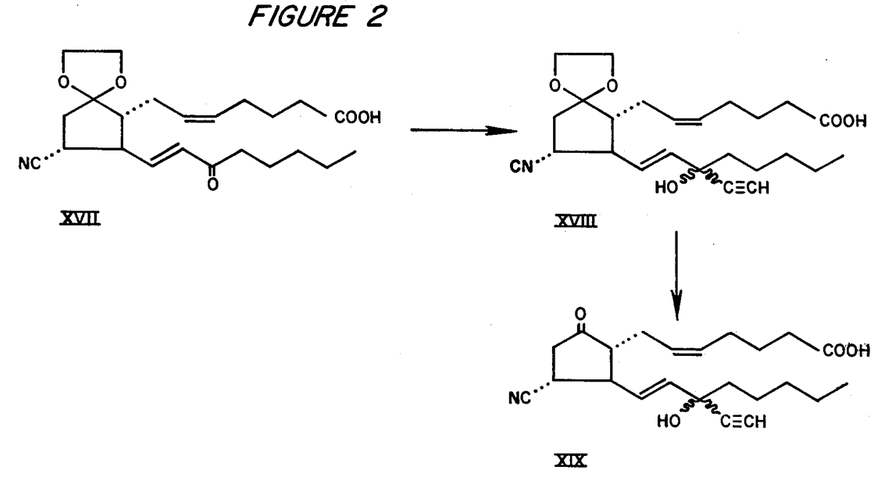

In describing the synthesis of compounds of Formula I wherein A is a cis double bond reference will be made to FIG. 2 wherein the formulae representing th specific embodiments are assigned Roman numerals for schematic identification. FIG. 2 illustrates the preparation of 7-(8α-cyano-7β-[(3RS)-3-ethynyl-3-hydroxy-trans-1-octenyl]-1,4-dioaspiro[4.4]non-6α-yl)-cis-5-heptenoic acid (XVIII) and 7-[3α-cyano-2β-(3-ethynyl-3-hydroxy-trans-1-octenyl)-5-oxo-1α-cyclopentyl]-cis-a-heptenoic acid (XIX), which are specific embodiments of Formula I wherein A is a cis double bond.

The starting material for the preparation of XVIII, namely 7-[8α-cyano-7β-(3-oxo-trans-1-octenyl)-1,4-dioxaspiro[4.4]non-6α-yl]-cis-5-heptenoic acid (XVII) is described in Belgian Patent 803,854, published Feb. 21, 1974. Treatment of XVII with ethynyl grignard reagent gives XVIII. XVIII may be isolated, if desired, by standard techniques, for example, by elution chromatography on silica gel. If XVIII is treated with aqueous perchloric acid while in solution in tetrahydrofuran XIX is obtained. If desired, XIX may be isolated by standard techniques. Elution chromatography on silica gel is convenient, and if used, the two products are obtained which are isomeric at the 15-position (prostaglandin numbering system).

3α-Cyano-2β-[(3S)-3-hydroxy-trans-1-octenyl]-5-oxo-1α-cyclopentaneheptanoic acid, (XX) a specific embodiment of Formula III is prepared from 7-[3α-cyano-2((3S)-3-hydroxy-trans-1-octenyl)-5-oxo-1α-cyclopentyl]-cis-5-heptenoic acid (XXI), which is disclosed in Belgian Patent 803,854 referenced hereinabove. Treatment of XXI with hydrogen at room temperature and atmosheric pressure in the presence of tris-(triphenylphosphine)-rhodium (I) chloride as a catalyst gives XX. If desired, XX may be isolated by elution chromatography on silica.

3α-Cyano-2β-[(3RS)-3-hydroxy-3-methyl-trans-1-octenyl]-5-oxo-1α-cyclopentane heptanoic acid (XXII) and 3α-cyano-5(RS)-hydroxy-2β-[(3RS)-3-hydroxy-3-methyl-trans-1-octenyl]-1α-cyclopentaneheptanoic acid XXIII, both specific embodiments of Formula IV, are prepared from 7-(3α-cyano-2β[(3RS)-3-hydroxy-3-methyl-trans-1-octenyl]-5-oxo-1α-cyclopentyl)-cis-5-heptenoic acid (XXIV). XXIV is described in Belgian Patent 803,854 referenced hereinabove. Treatment of XXIV with hydrogen at atmospheric pressure and room temperature in the presence of a Pd on charcoal catalyst gives XXII. If desired, XXII may be isolated by standard techniques. Elution chromatography is a convenient method. Treatment of XXII with sodium borohydride gives XXIII. If desired, XXIII may be isolated by standard techniques. Elution chromatography on silica gel is a convenient method.

It will be apparent to those skilled in the art that where during the preparation of compositions of the invention an oxo function is converted to a hydroxylic function, either through reduction or by introduction of a substituent onto the carbon atom, an assymetric carbon atom is created, and as a consequence these positions can have the substituents spatially oriented in either of two possible epimeric configurations. This situation will also arise when the starting material for a reaction sequence bears substituents on an assymetric carbon atom in either of the two possible epimeric configurations. The assymetric center may be either destroyed by further reaction or the epimers either separated or chemically manipulated to comprise one configuration to the substantial exclusion of the other. The symbol ⁓ where used in this specification is to indicate that both possible configurations at each particular position is intended and is included within the scope of the invention. Separation of the epimeric mixtures can, of course, be accomplished by methods well-known in the art.

The esters of formulas I, III and IV (R is alkyl) are prepared by standard methods, such as for example, by treating a solution of the free acids with diazomethane or other appropriate diazohydrocarbons, such as diazoethane, 1-diazo-2-ethylpentane, and the like. The alkali metal carboxylates of the invention can be prepared by mixing stoichiometrically equivalent amounts of the free acids of formula I, preferably in aqueous solution, with solutions of alkali metal bases, such as sodium, potassium, and lithium hydroxides or carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The term "alkyl or from about 1 to about 6 carbon atoms" when used herein and in the appended claims includes straight and branched chain hydrocarbon radicals, illustrative members of which are methyl, ethyl, n-propyl, i-propyl, n-butyl, t-butyl, n-pentyl, n-hexy, 3-methylpentyl, 2,3-dimethylbutyl, and the like. "Alkali metal" includes, for example, sodium, potassium, lithium, and the like. A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

wherein R¹, R², and R³, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms, or, when taken together with the nitrogen atom to which they are attached, any two of R¹, R², and R³ form part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethylidiethanolammonium, n-butylmonoethanolammonium tris(hydroxymethyl)-methylammonium, phenylmonoethanolammonium, and the like.

In using the compounds of the invention to produce bronchodilating effects in warm-blooded animals, they may be administered in a variety of dosage forms: oral, injectable, and oral inhalation. Oral inhalation administration is a preferred route because of its rapid onset of action, great potency, and specificity of action. The particular dosage to obtain the bronchodilating effect will vary with the particular compound employed, the particular animal involved, and the degree of bronchodilation desired. In the guinea pig, by the oral inhalation route, the dose to produce bronchodilation is from about 0.2 micrograms to about 100 micrograms, and preferably from about 5 to about 50 micrograms. The bronchodilation produced upon oral inhalation administration can be observed by the method or Rosenthale et al., Int. Arch. Pharmacol., 172, 91 (1968).

In using the compounds of the invention to produce antiinflammatory effects in warm-blooded animals, they may be administered subcutaneously. The particular dosage to obtain the antiinflammatory effect will vary with the particular compound employed and the degree of antiinflammatory response desired. The antiinflammatory response produced upon subcutaneous administration can be observed by the method described by Newbould, B. B. in Brit. J. Pharm. Chemoth., 21, 127 (1963) and Rosenthale, M. E., and Nagra, C. L. in Proc. Soc. Exp. Biol. and Med., 125, 149 (1967). In this procedure, adjuvant-induced arthritis is induced in rats by injection of dead mycobacteria into the hind footpad. The test compound is administered subcutaneously daily for sixteen consecutive days beginning with the day of injection. The injected foot swells rapidly during the first 4 to 6 days. Thereafter, the swelling subsides until the 8th day, and then it resumes. About 4 to 10 days after injection, the other hind paw (un-injected) becomes swollen and other inflammatory nodules may be found in the ear and tail. The swelling of the injected paw at day 4 is taken as an indication of an acute inflammatory response. The swelling of the same paw at day 16 is taken as a delayed inflammatory response. The swelling of the other hind paw at day 16 is taken as a delayed hypersensitivity reaction. Active antiinflammatory compounds reduce the swelling in either the acute and/or the delayed phases. Steroidal and non-steroidal antiinflammatory agents reduce swelling in the acute and/or the delayed phase, while immunosuppressives reduce swelling only in the delayed phase. The percent protection against swelling, as compared to non-treated controls, is calculated and is used as a measure of antiinflammatory activity.

The following examples further illustrate the best mode contemplated by the inventors for the practice of their invention:

EXAMPLE 1

7-[8α-Cyano-7β-((3S)-3-Hydroxy-Trans-1-Octenyl)-1,4-Dioxaspiro[4.4]Non-6α-Yl]-Cis-5-Heptenoic Acid A solution of 10.0 g. of 7-[8-cyano-7-((3S)-3-hydroxy-trans-1-oxtenyl)-1,4-dioxaspiro[4.4]non-6α-yl]-cis-5-heptenoic acid and 13.0 g. of potassium t-butoxide in 700 ml. of t-butanol was stirred at 25° under nitrogen for 40 hours. The reaction mixture was diluted with water, acidified with acetic acid and extracted with ether. After washing and drying, the extract was evaporated and the residue chromatographed on silica. Elution with 35% ethyl acetate in hexane followed by recrystallization from ether-pentane gave 3.0 g. of the title product, m.p. 58.5°–61° C., $\lambda_{max}^{KBr}$ 3.0, 3.4, 5.8, 8.5, 8.9, 9.65, 10.3 μ. NMR⁺: δ 6.72 (S, 2, OH), 5.65 (M, 2, 13 and 14-H), 5.40 (M, 2, 5 and 6-H), 4.18 (M, 1, 15-H), 3.92 (S, 4, ketal) ppm. Mass spectrum: M⁺ at m/e 405.2492 (theory 405.2514).

EXAMPLE 2

7-[3α-Cyano-2-((3S)-3-Hydroxy-Trans-1-Octenyl)-5-Oxo-1α-Cyclopentyl]-Cis-5-Heptenoic Acid An ice-cooled solution of 0.5 g. of 7-[8α-cyano-7((3S)-3-hydroxy-trans-1-octenyl)-1,4-dioxaspiro[4.4]non-6α-yl]-cis-5-heptenoic acid in 50 ml. of tetrahydrofuran was treated with 12.5 ml. of hydrochloric acid and stirred at 0° C. for 1 hour. The mixture was diluted with water, extracted with ether and the extract washed, dried and evaporated. Silica chromatography of the resulting residue with 35% ethyl acetate in hexane followed by recrystallization from ether-hexane gave 0.26 g. of the title product, m.p. 71°–73° C., $\lambda_{max}^{KBr}$ 3.0, 3.4, 5.7, 7.9, 8.55, 9.8, 10.3 μ. NMR: δ 7.0 (S, 2, OH), 5.82 (M, 2, 13 and 14-H), 5.50 (M, 2, 5 and 6-H), 4.28 (M, 1, 15-H) ppm.

Analysis for: $C_{21}H_{31}O_4N$ Calculated: C, 69.77; H, 8.63; N, 3.86; Found: C, 69.69; H, 8.83; N, 3.62.

EXAMPLE 3

3α-Cyano-2β-[(3S)-3-Hydroxy-Trans-1-Octenyl]-5-Oxo-1α-Cyclopentane Heptanoic Acid A solution of 0.4 g. of 7-[3α-cyano-2-((3S)-3-hydroxy-trans-1-oxtenyl)-5-oxo-1α-cyclopentyl]-cis-5-heptenoic acid and 0.4 g. of tris (triphenylphosphine)-rhodium (I) chloride in 60 ml. of 1:1 benzene-ethanol was hydrogenated at 25° and atmospheric pressure until 1 equivalent of hydrogen was absorbed. The mixture was concentrated under vacuum and the residue chromatographed on silica. Elution with 35% ethyl acetate in hexane followed by recrystallization from ether-hexane gave 0.112 g. of the title product, m.p. 90°–92° C., $\lambda_{max}^{KBr}$ 2.95, 3.5, 4.5, 5.75, 5.9, 7.1, 7.85, 8.15, 8.45, 10.35 μ. NMR: δ 6.38 (S, 2, OH), 5.70 (M, 2, 13 and 14-H), 4.18 (M, 1, 15-H) ppm.

Analysis for: $C_{21}H_{33}NO_4$ Calculated: C, 69.40; H, 9.15; N, 3.85; Found: C, 69.37; H, 9.18; N, 3.85.

EXAMPLE 4

7-[8α-Cyano-7β-((3RS)-3-Ethynyl-3-Hydroxy-Trans-1-Octenyl)-1,4-Dioxaspiro[4.4]Non-6α-Yl]-Cis-5-Heptenoic Acid A solution of 0.755 g. of 7-[8α-cyano-7β-(3-oxo-trans-1-octenyl)-1,4-dioxaspiro[4.4]non-6α-yl]-cis-5-heptenoic acid in 15 ml. of tetrahydrofuran was added to an ice-cooled solution of ethynyl magnesium bromide (made from 6.3 ml. of 3M methyl magnesium bromide and excess acetylene) in 60 ml. of tetrahydrofuran and stirred at 0° C. for 15 minutes. The reaction mixture was diluted with ammonium chloride solution, acidified with acetic acid and extracted with ether. After washing and drying, the extract was evaporated and the residue chromatographed on silica. Elution with 40% ethyl acetate in hexane gave 0.562 g. of the title product, $\lambda_{max}^{film}$ 3.05, 3.45, 4.5, 5.75, 8.7, 9.7 μ. NMR: δ 6.05 (OH), 5.70 (M, 13 and 14-H), 5.35 (M, 5 and 6-H), 3.97 (S, ketal), 2.56 (S, ethynyl-H) ppm. Mass spectrum: M⁺ at m/e 429 (theory 429).

EXAMPLE 5

7-[3α-Cyano-2β-(3-Ethynyl-3-Hydroxy-Trans-1-Octenyl)-5-Oxo-1α-Cyclopentyl]-Cis-5-Heptenoic Acid A solution of 0.295 g. of 7-[8α-cyano-7β-((3RS)-3-ethynyl-3-hydroxy-trans-1-octenyl)-1,4-dioxaspiro[4.4]non-6α-yl]-cis-5-heptenoic acid in 11.3 ml. of tetrahydrofuran was treated with 5.0 ml. of 3M aqueous perchloric acid and kept at 25° for 18 hours. The reaction mixture was diluted with ether, washed, dried and evaporated. Silica chromatography of the resulting residue with 40% ethyl acetate affected partial separation and gave 0.085 g. of a first fraction followed by 0.12 g. of a second fraction. Combination of the above crude fractions with equivalent material from other runs and separate rechromatography on a silica partition column [as described in J. Org. Chem., 37, 1810, 1818 (1972)] gave the title product as two products, epimeric at the 15-position (prostaglandin numbering) which exhibited identical spectra: $\lambda_{max}^{film}$ 3.0, 3.35, 4.4, 5.7, 7.1, 8.05, 8.6, 10.3 μ. NMR: δ 5.90 (M, 2, 13 and 14-H), 5.43 (M, 2, 5 and 6-H), 2.60 (S, ethynyl-H) ppm. Mass spectrum: M⁺ at m/e 385 (theory 385).

EXAMPLE 6

(3RS)-3-Cyano-2β-[(3R)-3-Hydroxy-Trans-1-Octenyl]-5-Oxo-1α-Cyclopentaneheptanoic Acid, Methyl Ester, Acetate A solution of 3.0 g. of 7-((3RS)-3-cyano-2β-[(3R)-3-hydroxy-trans-1-octenyl]-5-oxo-1α-cyclopentyl)-cis-5-heptenoic acid, methyl ester, acetate and 1.5 g. of tris(-triphenylphosphine)rhodium (I) chloride was hydrogenated in 160 ml. of 1:1 benzene-ethanol at 25° C. and atmospheric pressure until 1 equivalent of hydrogen was absorbed. The mixture was evaporated and the residue chromatographed on silica. Elution with 20% ethyl acetate in hexane gave 2.3 g. of the title product as an oil, $\lambda_{max}^{film}$ 3.40, 4.50 (weak), 5.75, 7.25, 8.0, 9.8, 10.3 μ. NMR: δ 5.72 (M, 2, 13 and 14-H), 5.32 (M, 1, 15-H), 3.68 (S, 3, OCH₃), 2.05 (S, acetate) ppm.

EXAMPLE 7

(8RS)-8-Cyano-7β-[(3R)-3-Hydroxy-Trans-1-Octenyl]-1,4-Dioxaspiro[4.4]Nonane-6α-Heptanoic Acid, Methyl Ester, Acetate A solution of 2.3 g. of (3RS)-3-cyano-2β-[(3R)-3-hydroxy-trans-1-octenyl]-5-oxo-1α-cyclopentaneheptanoic acid, methyl ester, acetate and 0.15 g. of p-toluenesulfonic acid in 150 ml. of benzene and 15 ml. of ethylene glycol was refluxed with a water separator for 24 hours. After dilution with water and extraction with ether, the ether extract was washed, dried, and evaporated. Silica chromatography of the residue with 20% ethyl acetate in hexane afforded 1.9 g. of the title product as an oil, $\lambda_{max}^{film}$ 3.4, 4.45 (weak), 5.75, 7.3, 8.05, 9.8 μ. NMR: δ 5.68 (M, 2, 13 and 14-H), 5.35 (M, 1, 15-H), 3.98 (S, 4, ketal), 3.70 (S, 3, OCH₃), 2.08 (S, acetate) ppm. Mass spectrum: M⁺ at m/e 463 (theory 463), M⁺-OAc at m/e 404.2794 (theory 404.2800).

EXAMPLE 8

(8RS)-8-Cyano-7β-[(3R)-3-Hydroxy-Trans-1-Octenyl]-1,4-Dioxaspiro[4.4]Nonane-6α-Heptanoic Acid A solution of 18 g. of (8RS)-8-cyano-7β-[(3R)-3-hydroxy-trans-1-octenyl]-1,4-dioxaspiro[4.4]nonane-6α-heptanoic acid, methyl ester, acetate in 1 liter of methanol was treated with 800 ml. of 1N sodium hydroxide and kept at 25° for 0.5 hours. The mixture was diluted with water, acidified with acetic acid and extracted with ether. After washing and drying, the extract was evaporated to obtain 16.7 g. of the title product as an oil, $\lambda_{max}^{film}$ 3.0 (shoulder), 4.45 (weak), 5.8, 8.65, 9.8, 10.3, 10.5 μ. NMR: δ 7.55 (S, 2, OH), 5.63 (M, 2, 13 and 14-H), 4.12 (M, 1, 15-H), 3.93 (S, 4, ketal ppm.

EXAMPLE 9

8α-Cyano-7β-[(3R)-3-Hydroxy-Trans-1-Octenyl]-1,4-Dioxaspiro[4.4]Nonane-6α-Heptanoic Acid A solution of 16.5 g. of (8RS)-8-cyano-7β-[(3R)-3-hydroxy-trans-1-octenyl]-1,4-dioxaspiro[4.4]nonane-6α-heptanoic acid in 1 liter of t-butanol was treated with 24 g. of potassium t-butoxide and stirred at 25° C. for 22 hours. The mixture was diluted with water, acidified with acetic acid and extracted with ether. After washing and drying, the extract was evaporated and the residue chromatographed on silica. Elution with 35% ethyl acetate in hexane followed by two recrystallizations from ether-pentane gave 4.85 g. of the title product, m.p. 79°–80.5° C., $\lambda_{max}^{KBr}$ 3.0, 3.4, 4.5 (weak), 5.85, 7.8, 8.5, 9.15, 9.75, 10.3 μ. NMR: δ6.92 (S, 2, OH), 5.65 (M, 2, 13 and 14-H), 4.17 (M, 1, 15-H), 3.95 (S, 4, ketal) ppm.

Analysis for: $C_{23}H_{37}NO_5$ Calculated: C, 67.78; H, 9.16; N, 3.44; Found: C, 67.94; H, 9.63; N, 3.44; Mass spectrum: M$^+$ at m/e 407.2703 (theory 407.2670).

EXAMPLE 10

8α-Cyano-7β-(3-Oxo-Trans-1-Octenyl)-1,4-Dioxaspiro[4.4]Nonane-6α-Heptanoic Acid

An ice-cooled solution of 4.75 g. of 8α-cyano-7β-[(3R)-3-hydroxy-trans-1-octenyl]-1,4-dioxaspiro[4.4]nonane-6α-heptanoic acid in 150 ml. of acetone was treated with Jones reagent until the orange color persisted. After stirring at 0° for 0.5 hours, the mixture was treated with methanol, dilute sodium bicarbonate until basic and acidified with acetic acid. Following extraction with ether, the extract was washed, dried and evaporated to obtain 4.5 g. of the title product as an oily solid, $\lambda_{max}^{KBr}$ 3.2, 3.45, 4.5 (weak), 5.8, 5.9, 6.15, 7.7, 8.55, 9.7 μ. NMR: δ 10.6 (S, 1, OH), 6.65 (dd, 1, J=15.7 and 7.5, 13-H), 6.23 (d, 1, J=15.7, 14-H), 3.95 (S, 4, ketal) ppm. Mass spectrum: M$^+$ at m/e 405.2559 (theory 405.2514).

EXAMPLE 11

8α-Cyano-7β-[(3RS)-3-Ethynyl-3-Hydroxy-Trans-1-Octenyl]-1,4-Dioxaspiro[4.4]Nonane-6α-Heptanoic Acid A solution of 2.2 g. of 8α-cyano-7β-(3-oxo-trans-1-octenyl)-1,4-dioxaspiro[4.4]nonane-6α-heptanoic acid in 50 ml. of tetrahydofuran was added to an ice-cooled solution of ethynyl magnesium bromide (made from 20 ml. of 3M methyl magnesium bromide and excess acetylene) in 185 ml. of tetrahydrofuran. After stirring at 0° for 0.5 hours, the mixture was diluted with ammonium chloride solution, acidified with acetic acid and extracted with ether. Following washing and drying, the extract was evaporated to obtain 2.2 g. of the title product as an oil, $\lambda_{max}^{film}$ 3.05, 3.45, 4.45 (weak), 5.85, 8.65, 9.8, 10.3, 10.6 μ. NMR: δ 6.8 (M, 2, OH), 5.75 (M, 2, 13 and 14-H), 3.93 (S, 4, ketal), 2.58 (S, C ≡ C—H) ppm. Mass spectrum: M$^+$ at m/e 431.2697 (theory 431.2670).

EXAMPLE 12

3α-Cyano-2β-[(3RS)-3-Ethynyl-3-Hydroxy-Trans-1-Octenyl]-5-Oxo-1α-Cyclopentane-Heptanoic Acid A solution of 2.0 g. of 8α-cyano-7β-[(3RS)-3-ethynyl-3-hydroxy-trans-1-octenyl]-1,4-dioxaspiro[4.4]nonane-6α-heptanoic acid in 80 ml. of tetrahydrofuran was treated with 35 ml. of 3M perchloric acid and kept at 25° for 18 hours. The mixture was diluted with ether, washed, dried and evaporated. Silica chromatography of the residue with 35% ethyl acetate in hexane gave 0.15 g. of the title product as an oil, $\lambda_{max}^{film}$ 3.05, 3.4, 4.5 (weak), 5.75, 5.85, 8.7, 10.35 μ. NMR: δ 5.90 (M, 2, 13 and 14-H), 2.60 (S, C ≡ C—H) ppm. Mass spectrum: M$^+$ at m/e 387.2432 (theory 387.2409).

EXAMPLE 13

8α-Cyano-7β-(3-Oxo-Octyl)-1,4-Dioxaspiro[4.4]Nonane-6α-Heptanoic Acid

A solution of 2.1 g. of 8α-cyano-7β-(3-oxo-trans-1-octenyl)-1,4-dioxaspiro[4.4]nonane-6α-heptanoic acid in 50 ml. of ethyl acetate was added to a prehydrogenated mixture of 0.22 g. of 10% Pd/C in 50 ml. of ethyl acetate and the mixture hydrogenated at 25°C. and atmospheric pressure until 1 equivalent of hydrogen was absorbed. The mixture was filtered, evaporated and the residue chromatographed on silica. Elution with 30% ethyl acetate in hexane afforded 1.7 g. of the title product as a solid, m.p. 62°–65° C., $\lambda_{max}^{KBr}$ 3.45, 4.5 (weak), 5.8, 7.55, 8.65, 9.7, 10.55 μ. NMR: δ 10.7 (S, 1, OH), 3.90 (S, 4, ketal) ppm.

Analysis for: $C_{23}H_{37}NO_5$ Calculated: C, 67.78; H, 9.15; N, 3.44; Found: C, 67.56; H, 9.77; N, 3.56; Mass spectrum: M$^+$ —$C_5H_{11}$ at m/e 336.1832 (theory 336.1810).

EXAMPLE 14

8α-Cyano-7β-[(3RS)-3-Ethynyl-3-Hydroxyoctyl]-1,4-Dioxaspiro[4.4]Nonane-6α-Heptanoic Acid A solution of 1.6 g. of 8α-cyano-7β-(3-oxo-octyl)-1,4-dioxaspiro[4.4]nonane-6α-heptanoic acid in 50 ml. of tetrahydrofuran was added to an ice-cooled solution of ethynyl magnesium bromide (made from 20 ml. of 3M methyl magnesium bromide and excess acetylene ) in 185 ml. of tetrahydrofuran. After stirring at 0° C. for 0.5 hours, the mixture was diluted with ammonium chloride solution, acidified with acetic acid and extracted with ether. Following washing and drying, the extract was evaporated to obtain 1.65 g. of the title product as an oil, $\lambda_{max}^{film}$ 3.1 (shoulder), 3.45, 4.45 (weak), 5.8, 6.85, 8.65, 9.65 μ. NMR: δ 6.4 (M, 2, OH), 3.92 (S, 4, ketal), 2.50 (S, C C—H) ppm. Mass spectrum: M$^+$—$C_5H_{11}$ at m/e 362.1991 (theory 362.1966).

EXAMPLE 15

3α-Cyano-2β[(3RS)-3-Ethynyl-3-Hydroxyoctyl]-5-Oxo-1α-Cyclopentaneheptanoic Acid

A solution of 1.5 g. of 8α-cyano-7β-[(3RS)-3-ethynyl-3-hydroxyoctyl]-1,4-dioxaspiro[4.4]nonane-6α-heptanoic acid in 80 ml. of tetrahydrofuran was treated with 30 ml. of 3M perchloric acid and kept at 25° C for 4 hours. The mixture was diluted with ether, washed, dried and evaporated. Silica chromatography of the residue with 30% ethyl acetate in hexane afforded 1.0 g. of the title product as an oil, $\lambda_{max}^{film}$ 3.1, 3.5, 4.45 (weak), 5.85, 7.1, 8.65, 10.7 μ. NMR: δ 6.42 (M, OH), 2.53 (S, C C—H) ppm. Mass spectrum: M$^+$—$C_5H_{11}$ at m/e 318 (theory 318), M$^+$—$C_5H_{11}$—$H_2O$ at m/e 300.1648 (theory 300.1599).

EXAMPLE 16

3α-Cyano-2β-[(3RS)-3-Hydroxy-3-Methyl-Trans-1-Octenyl]-5-Oxo-1α-Cyclopentane Heptanoic Acid A solution of 0.426 g. of 7-[3α-cyano-2β-[(3RS)-3-hydroxy-3-methyl-trans-1-octenyl]-5-oxo-1α-cyclopentyl]-cis5-heptenoic acid in 10 ml. of ethyl acetate was added to a prehydrogenated mixture of 0.09 g. of 10% Pd/C in 10 ml. of ethyl acetate and hydrogenated at 25° C. and atmospheric pressure until 1 equivalent of hydrogen was absorbed. Removal of the catalyst and evaporation of the solvent followed by silica chromatography of the residue with 30% ethyl acetate in hexane gave 0.38 g. of the title product as an oil, $\lambda_{max}^{film}$ 3.0 (shoulder), 3.45, 4.45 (weak), 5.7, 5.8, 6.8, 8.2, 10.3 $\mu$. NMR: $\delta$ 6.42 (S, 2, OH), 5.87 (2, M, 13 and 14-H) ppm. Mass spectrum: $M^+$ at m/e 377 (theory 377), $M^+$ —$H_2O$ at m/e 359.2447 (theory 359.2460).

EXAMPLE 17

The in vivo antiinflammatory activity of the compounds is elicited and demonstrated by employing the following procedures:

Male rats are randomly dispersed into groups. One group is injected with a mineral oil suspension of heat-killed tubercle bacilli in the subplantar portion of the right hind paw (day 0). On the same day, a single dose of the test compound is administered subcutaneously. Groups of normal and positive arthritic rats are given vehicle only. Each rat is given a single dose daily for a total of sixteen days. On day 4, the volume of the injected (right) foot is measured by means of a mercury plethysmograph. On day 16, the volumes of both the injected, right foot and the left hind foot are measured. The ability of the test compound to protect against acute and delayed swelling is measured by calculating the per cent decrease in volume of the test animals as compared to controls. When tested by the above procedures, 3α-cyano-5(RS)-hydroxy-2β[(3RS)-3-hydroxy-3-methyl-trans-1-oxtenyl]-1α-cyclopentaneheptanoic acid gave results as follows:

| Daily Dose S. C. | % Inhibition of Swelling | | |
|---|---|---|---|
| (mg/kg.) | Day 4 Rt. Paw | Day 16 Rt. Paw | Left Paw |
| 0.5 | 25 | 31 | 35 |

When the compounds of the invention are employed as antiinflammatory agents, they may be administered alone or in combination with pharmaceutically acceptable carriers, the proportion of which is determined by the solubility and chemical nature of the compound, chosen route of administration, and standard pharmaceutical practice. For example, they may be injected parenterally, e.g. intramuscularly. For parenteral administration, they may be used in the form of a sterile solution or suspensions containing other solutes, for example, enough saline or glucose to make the solution isotonic.

The subject matter which applicants regard as their invention is particularly pointed out and distinctly claimed as follows:

1. A compound of the formula:

wherein R is hydrogen, lower alkyl of from 1 to about 6 carbon atoms, alkali metal, or a pharmaceutically acceptable cation derived from ammonia or a primary amine; and A is a cis double bond and B is a trans double bond; A is a single bond and B is a trans double bond; or A is a single bond, and B is a single bond.

2. A compound as defined in claim 1, which is 7-[3α-cyano-2β-(3-ethynyl-3-hydroxy-trans-1-octenyl)-5-oxo-1α-cyclopentyl]-cis-5-heptenoic acid.

3. A compound as defined in claim 1 which is 3α-cyano-2β-[(3RS)-3-ethynyl-3-hydroxy-trans-1-octenyl]-5-oxo-1α-cyclopentaneheptanoic acid.

4. A compound as defined in claim 1 which is 3α-cyano-2β-[(3RS)-3-ethynyl-3-hydroxyoctyl]-5-oxo-1α-cyclopentaneheptanoic acid.

* * * * *